United States Patent [19]
Arai

[11] Patent Number: 5,590,167
[45] Date of Patent: Dec. 31, 1996

[54] DIGITAL PANORAMIC X-RAY IMAGING APPARATUS

[75] Inventor: Yoshinori Arai, Tokyo, Japan

[73] Assignee: J. Morita Manufacturing Corporation, Kyoto, Japan

[21] Appl. No.: 613,383

[22] Filed: Mar. 7, 1996

[30] Foreign Application Priority Data

Mar. 10, 1995 [JP] Japan .................................. 7-051106
Feb. 29, 1996 [JP] Japan .................................. 8-042952

[51] Int. Cl.⁶ .................................................. A61B 6/14
[52] U.S. Cl. ............................ 378/38; 378/39; 378/22; 250/583
[58] Field of Search .......................... 378/38, 39, 40, 378/21, 22, 32, 191, 190, 189; 250/583

[56] References Cited

U.S. PATENT DOCUMENTS

| 4,439,866 | 3/1984 | Kato et al. .................... 250/583 |
| 4,754,137 | 6/1988 | Saotome et al. ................ 250/38 |

FOREIGN PATENT DOCUMENTS

| 60-149042 | 8/1985 | Japan ...................... G03B 42/02 |
| 61-134687 | 6/1986 | Japan ...................... G01T 1/115 |
| 62-213363 | 9/1987 | Japan ...................... H04N 1/04 |
| 63-259636 | 10/1988 | Japan ..................... G03B 42/02 |
| 1-241536 | 9/1989 | Japan ...................... G03B 42/02 |
| 4-320244 | 11/1992 | Japan ..................... G03B 42/02 |
| 5-264475 | 10/1993 | Japan ...................... G01N 23/04 |

Primary Examiner—Don Wong
Attorney, Agent, or Firm—Koda and Androlia

[57] ABSTRACT

A digital panoramic X-ray imaging apparatus comprising an X-ray generator for irradiating a subject P with X-rays, an X-ray imaging device for detecting an image of X-rays having passed through the subject P and a swivel member for supporting the X-ray generator and the X-ray imaging device and for rotating the X-ray generator and the X-ray imaging device around subject P is disclosed. The X-ray imaging device comprises a rotation drum disposed in parallel with the rotation shaft of the swivel member, a storage fluorescent sheet disposed on the circumferential surface of the rotation drum, a laser for irradiating the storage fluorescent sheet with excitation light and a photomultiplier for receiving accelerated-phosphorescence emission caused from the storage fluorescent sheet by excitation light irradiation. Primary scanning is performed by rotating the rotation drum, and secondary scanning is performed by moving the laser and the photomultiplier in the axial direction of the rotation drum.

With this structure, a compact, lightweight digital panoramic X-ray imaging apparatus is obtained.

5 Claims, 9 Drawing Sheets

DIGITAL PANORAMIC X-RAY IMAGING APPARATUS

BACKGROUND OF THE INVENTION

1. Field of the Invention

The present invention relates to a digital panoramic X-ray imaging apparatus.

2. Description of the Related Art

Conventionally, a storage fluorescent substance (accelerated-phosphorescence fluorescent substance) is known, which stores part of the energy of radiant rays, when the fluorescent substance is irradiated with the radiant rays such as X-rays, and performs accelerated-phosphorescence emission depending on the level of the stored energy when the fluorescent substance is then irradiated with excitation light, such as visible light.

Japanese Unexamined Patent Application JPA 60-149042 (1985) discloses a radiant ray image information reading apparatus wherein a storage fluorescent sheet is wound around a rotation drum, and a plurality of reading heads, each being composed of an excitation light source and a light-receiving device, are used to perform secondary scanning in a direction nearly parallel to the shaft of the drum.

Japanese Unexamined Patent Application JPA 62-213363 (1987) discloses a radiant ray image information reading apparatus, wherein a storage fluorescent substance is formed on the circumferential surface of a rotation drum, and a reading head composed of an excitation light source, an optical wave guide and a light-receiving device is disposed in a reflection or transmission arrangement to perform secondary scanning in a direction nearly parallel to the shaft of the drum.

Japanese Unexamined Patent Application JPA 63-259636 (1988) discloses a radiant ray image information reading apparatus, wherein a storage fluorescent sheet is wound around a plurality of rollers in an endless belt form, an image reading portion composed of an excitation light source and a light-receiving device is integrated with an erasing portion for releasing residual energy before image recording to form an image reading unit, and the image reading unit can be rotated so as to have a predetermined positional relationship with a radiant ray source.

Japanese Unexamined Patent Application JPA 1-241536 (1989) discloses an X-ray image detection apparatus comprising an X-ray generator, a storage fluorescent sheet, a sheet holder, an excitation light irradiation source, a fluorescence detector, an after-image eraser and an imaging controller.

Japanese Unexamined Patent Application JPA 4-320244 (1992) discloses a radiant ray image information reading apparatus, wherein a storage fluorescent sheet is held on a rotation drum, a scanning reading unit for partially performing primary scanning with excitation light in the width direction of the sheet and for detecting accelerated-phosphorescence emission is provided, and the scanning reading unit moves relative to the primary scanning direction.

Japanese Unexamined Patent Application JPA 5-264475 (1993) discloses an industrial computerized tomographic imaging apparatus, wherein a drum-type imaging plate (storage fluorescent substance) is used.

Japanese Unexamined Patent Application JPA 61-134687 (1986) discloses a radiant ray intensity distribution measuring apparatus, wherein a heat luminescence sheet is wound around a rotation drum and laser beam scanning is performed to detect fluorescent intensity distribution by using a photomultiplier.

However, in Japanese Unexamined Patent Application JPA 63-259636 where a storage fluorescent sheet is wound around a plurality of rollers in an endless belt form, it is difficult to realize a viable apparauts because the durability of the fluorescent sheet is low.

In Japanese Unexamined Patent Application JPA 60-149042, the photon efficiency in the optical system of the reading head is only a few percent because of a long distance between the accelerated-phosphorescence emission point and the light-receiving device. In addition, a plurality of reading heads are necessary. Consequently, the entire apparatus becomes complicated and large.

In other prior art, the entire apparatus is large and not suited for dental panoramic imaging, wherein an X-ray generator and an X-ray imaging device are to be rotated around a subject.

SUMMARY OF THE INVENTION

The object of the present invention is to provide a digital panoramic X-ray imaging apparatus which is compact in size and lightweight.

The digital panoramic X-ray imaging apparatus of the invention for performing tomographic imaging along a predetermined tomographic plane of a subject, comprises:

an X-ray generator for irradiating a subject with X-rays;

an X-ray imaging device for detecting an image of X-rays having passed through the subject; and a swivel member for supporting the X-ray generator and the X-ray imaging device and for rotating the X-ray generator and the X-ray imaging device around the subject, characterized in that the X-ray imaging device comprises:

a rotation drum disposed in parallel with the rotation shaft of the swivel member;

a storage fluorescent sheet disposed on the circumferential surface of the rotation drum;

an excitation light source for irradiating the storage fluorescent sheet with excitation light;

a light-receiving portion for receiving accelerated-phosphorescence emission generated from the storage fluorescent sheet by excitation light irradiation;

a rotation drive portion for performing primary scanning by rotating the rotation drum; and a linear drive portion for performing secondary scanning by moving the excitation light source and the light-receiving portion in the axial direction of the rotation drum.

In accordance with the invention, a tomographic image along a predetermined tomographic plane is recorded on the storage fluorescent sheet by irradiating a subject with X-rays while the X-ray generator is rotated around the subject and by rotating the storage fluorescent sheet provided on the circumferential surface of the rotation drum at a low speed. Primary scanning is then performed by excitation light irradiation while the rotation drum is rotated. Accelerated-phosphorescence emission is generated and received and then converted into an image signal. In addition, secondary scanning is performed by moving the excitation light source and the light-receiving portion in the axial direction of the rotation drum. In this way, the two-dimensional scanning of the entire sheet surface can be accomplished and the tomographic image recorded on the storage fluorescent sheet can be read. Moreover, since the storage fluorescent sheet is formed in a cylindrical shape, less space is required for sheet movement, thereby enabling to make the apparatus compact.

Furthermore, the digital panoramic X-ray imaging apparatus of the invention for performing tomographic imaging along a predetermined tomographic plane of a subject, comprises:

an X-ray generator for irradiating the subject with X-rays;

an X-ray imaging device for detecting an image of X-rays having passed through the subject; and a swivel member for supporting the X-ray generator and the X-ray imaging device and for rotating the X-ray generator and the X-ray imaging device around the subject, characterized in that the X-ray imaging device comprises:

a light-transmissive rotation drum disposed in parallel with the rotation shaft of the swivel member;

a storage fluorescent sheet disposed on the circumferential surface of the rotation drum;

an excitation light source provided inside the rotation drum to irradiate the storage fluorescent sheet with the excitation light;

a light-receiving portion provided outside the rotation drum to receive accelerated-phosphorescence emission generated from the storage fluorescent sheet by excitation light irradiation;

a rotation drive portion for performing primary scanning by rotating the rotation drum; and first and second linear drive portions for performing secondary scanning by moving the excitation light source and the light-receiving portion in the axial direction of the rotation drum in synchronization with each other.

Furthermore, in accordance with the invention, after the tomographic image is recorded on the storage fluorescent sheet as described above, primary scanning is performed by excitation light irradiation from the inside of the light-transmissive rotation drum while the rotation drum is rotated. Accelerated-phosphorescence emission is generated, received and then converted into an image signal. By disposing the excitation light source and the light-receiving portion in a transmissive arrangement, the light-receiving portion can be placed close to the sheet, thereby significantly improving the light-receiving efficiency of the accelerated-phosphorescence emission. In addition, secondary scanning is performed by moving the excitation light source and the light-receiving portion in the axial direction of the rotation drum in synchronization with each other. In this way, the two-dimensional scanning of the entire sheet surface can be accomplished and the tomographic image recorded on the storage fluorescent sheet can be read. Moreover, since the storage fluorescent sheet is formed in a cylindrical shape, less space is required for sheet movement, thereby enabling to make the apparatus compact.

Furthermore, the digital panoramic X-ray imaging apparatus of the invention for performing tomographic imaging along a predetermined tomographic plane of a subject, comprises:

an X-ray generator for irradiating the subject with X-rays;

an X-ray imaging device for detecting an image of X-rays having passed through the subject; and a swivel member for supporting the X-ray generator and the X-ray imaging device and for rotating the X-ray generator and the X-ray imaging device around the subject, characterized in that the X-ray imaging device further comprises:

a rotation drum disposed in parallel with the rotation shaft of the swivel member;

a storage fluorescent sheet disposed on the circumferential surface of the rotation drum;

an excitation light source for generating excitation light;

a scanning optical system for irradiating the storage fluorescent sheet with the excitation light from the excitation light source and for performing primary scanning in the axial direction of the rotation drum;

a light-receiving portion for receiving accelerated-phosphorescence emission generated from the storage fluorescent sheet by excitation light irradiation; and a rotation drive portion for performing secondary scanning by rotating the rotation drum.

Furthermore, in accordance with the invention, X-ray imaging and primary scanning can be performed simultaneously by excitation light irradiation from the scanning optical system in the axial direction of the rotation drum while the tomographic image is recorded on the storage fluorescent sheet. Accelerated-phosphorescence emission is generated, received and then converted into an image signal. In addition, the secondary scanning is performed by rotating the rotation drum. In this way, the two-dimensional scanning of the entire sheet surface can be accomplished and the tomographic image recorded on the storage fluorescent sheet can be read. Moreover, since the storage fluorescent sheet is formed in a cylindrical shape, less space is required for sheet movement, thereby enabling to make the apparatus compact.

Furthermore, the apparatus of the invention comprises:

a primary slit for regulating an X-ray irradiation region in which a subject is irradiated with X-rays;

a primary slit shape changing means for changing the opening shape of the primary slit;

a secondary slit for regulating an X-ray detection region in which X-rays having passed through the subject are detected;

a secondary slit shape changing means for changing the opening shape of the secondary slit; and a scanning region setting means for setting the scanning region of the rotation drum, wherein the opening shapes of the primary and secondary slits and the scanning region of the rotation drum can be changed depending on the imaging mode.

Furthermore, in accordance with the invention, since the opening shapes of the primary and secondary slits and the scanning region of the rotation drum can be changed depending on the imaging mode, partial reading is possible, and necessary portions of image information can be taken out promptly.

The invention is characterized in that an X-ray sensor is disposed in the rotation drum and that the dosage of X-rays generated from the X-ray generator is controlled depending on the output from the X-ray sensor.

In accordance with the invention, since an X-ray sensor is disposed in the rotation drum and the dosage of X-rays generated from the X-ray generator is controlled depending on the output of the X-ray sensor, imaging is possible in proper x-ray imaging conditions.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Figure 1:
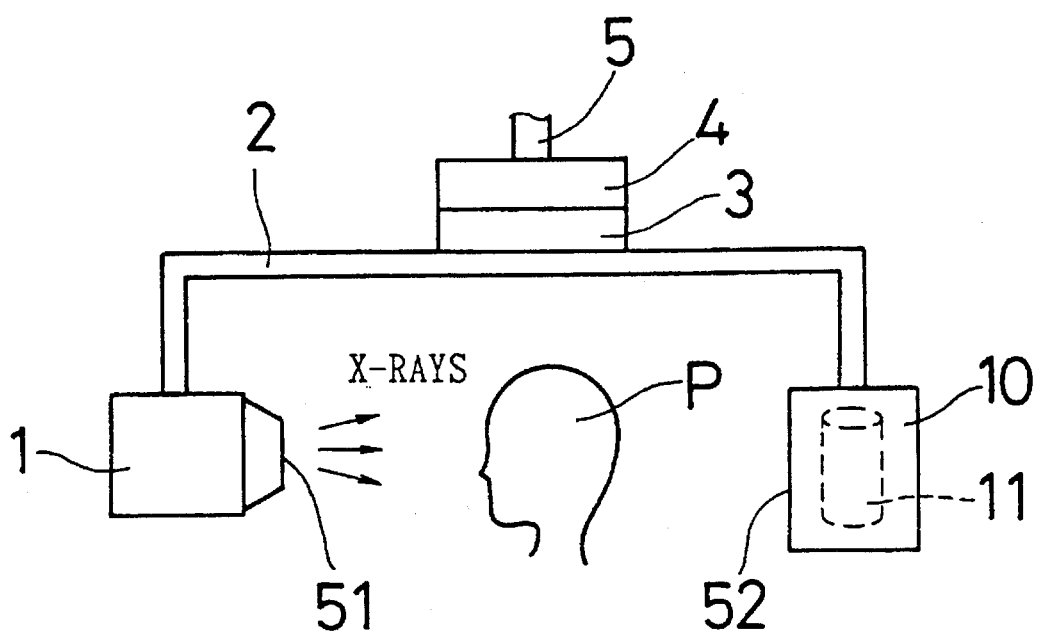
FIG. 1 is an overall view showing a digital panoramic X-ray imaging apparatus in accordance with the present invention.

Now referring to the drawings, preferred embodiments of the invention are described below.

First Embodiment

FIG. 1 is an overall view showing the construction of a digital panoramic X-ray imaging apparatus in accordance with the invention. At both ends of a swivel member 2 (such as a rotary arm), an X-ray generator 1 and an X-ray imaging device 10 are disposed opposite to each other. The X-ray generator 1 comprises an X-ray tube, a primary slit 51, etc. and irradiates a subject P with an X-ray beam having a vertically long slit shape. The X-ray imaging device 10 receives an image of X-rays having passed through the subject P and records the X-ray image on a storage fluorescent sheet 11 having a cylindrical shape by way of a secondary slit 52. The storage fluorescent sheet 11 has a circumstantial length of 300 mm and a width of 150 mm, for example, so as to correspond to the dimensions of the currently used X-ray panoramic film, and is provided on the circumstantial surface of a rotation drum disposed in parallel with the rotation shaft of the swivel member 2. The sheet 11 rotates at a constant speed during X-ray imaging and image reading.

The swivel member 2 is supported by a stationary arm 5 via a rotation table 3 and an X-Y table 4. The rotation position, rotation speed and rotation center of the swivel member 2 are controlled so that a tomographic image can be taken along a predetermined tomographic plane of the subject P.

Figure 2:
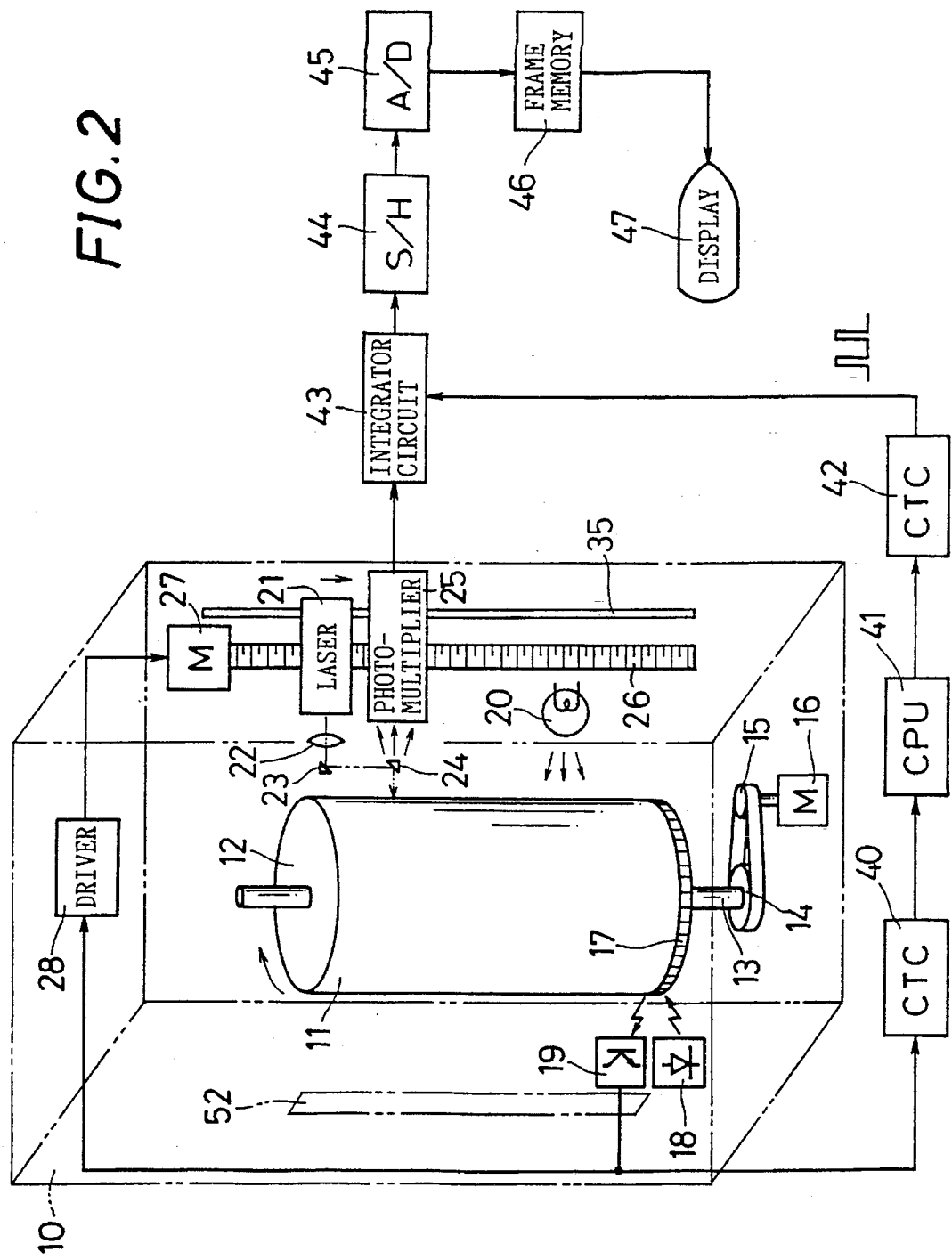
FIG. 2 is a view showing the construction of a first embodiment of the invention.

FIG. 2 is a view showing the construction of a first embodiment of the invention. In the X-ray imaging device 10, the storage fluorescent sheet 11 is provided on the circumstantial surface of a rotation drum 12, and a shaft 13 of the rotation drum 12 is driven by a motor 16 via pulleys 14, 15. An optical encoder 17 having streaks at regular intervals is provided at a circumstantial surface end portion of the rotation drum 12. A photosensor composed of a photodiode 18 and a phototransistor 19 generates a pulse signal corresponding to the rotation angle of the optical encoder 17.

A laser 21, such as a semiconductor laser, is used as an excitation light source for irradiating the storage fluorescent sheet 11 with excitation light. The excitation light from the laser 21 is converged by a lens 22, reflected by small triangular prisms 23, 24, and enters the storage fluorescent sheet 11 nearly perpendicularly. Accelerated-phosphorescence emission is generated from the portion irradiated with the excitation light depending on the level of the X-ray energy stored in the storage fluorescent sheet 11. The accelerated-phosphorescence emission is received by a photomultiplier 25 disposed close to the storage fluorescent sheet 11. An optical filter for shutting off the excitation light and allowing only the accelerated-phosphorescence emission to pass through is provided on the light-receiving surface of the photomultiplier 25.

The laser 21 and the photomultiplier 25 are integrally mounted on a screw shaft 26, while being unable to rotate around a support member 35, yet slidingly movable in the axial direction of the shaft 26, and moved linearly at a constant speed in the axial direction of the rotation drum 12 by the rotation of a motor 27 to perform secondary scanning during reading. On the other hand, primary scanning during reading is performed by the rotation of the rotation drum 12. After the two-dimensional scanning of the storage fluorescent sheet 11 is completed, an eraser lamp 20 turns on as the rotation drum 12 rotates, and residual X-ray energy is erased from the entire surface.

The pulse signal from the photosensor is supplied to a motor driver 28 for driving the motor 27 so as to control the rotation drum 12 and the screw shaft 26 in synchronization with each other. The pulse signal is also supplied to an integrator circuit 43 via a CTC (counter timer circuit) 40, a CFU (central processing unit) 41 and a CTC (counter timer circuit) 42.

The image signal converted into an electrical signal by the photomultiplier 25 is supplied to the integrator circuit 43 and integrated in synchronization with the above-mentioned pulse signal, sampled by an S/H (sample-and-hold) circuit 44, converted into digital data by an A/D (analog/digital converter) circuit 45, and stored in a frame memory 46. The image data stored in the frame memory 46 is indicated on a display 47, such as a CRT (cathode ray tube).

Next, recording operation is described below. During X-ray imaging, the laser 21, the photomultiplier 25, the eraser lamp 20, etc. stop operating, and the rotation drum 12 makes one revolution at a low speed (in 15 seconds, for example) in synchronization with one revolution of the swivel member 2 shown in FIG. 1. This synchronization is performed so that the X-ray movement speed at the tomographic plane of the subject P is equal to the circumstantial surface movement speed of the rotation drum 12. As a result, the X-rays from a secondary slit 52 enter the X-ray imaging device 10, and a desired tomographic image is recorded on the storage fluorescent sheet 11.

Next, image reading operation is described below. The rotation drum 12 rotates at a high speed of 1024 rpm, for example, and the laser 21 and the photomultiplier 25 move by 0.1 mm, for example, as the rotation drum 12 makes one revolution. The X-ray energy stored in the storage fluorescent sheet 11 is converted into accelerated-phosphorescence emission by excitation light. The accelerated-phosphorescence emission is converted into an electrical signal depending on the intensity of the accelerated-phosphorescence emission by the photomultiplier 25. The tomographic image thus taken is read as a time series image signal, stored in the frame memory 46 as digital data, subjected to a desired signal processing and displayed.

After a series of reading operations, the eraser lamp 20 turns on, the rotation drum 12 rotates, and residual X-ray energy is released so as to be ready for the next X-ray imaging.

Second Embodiment

Figure 3:
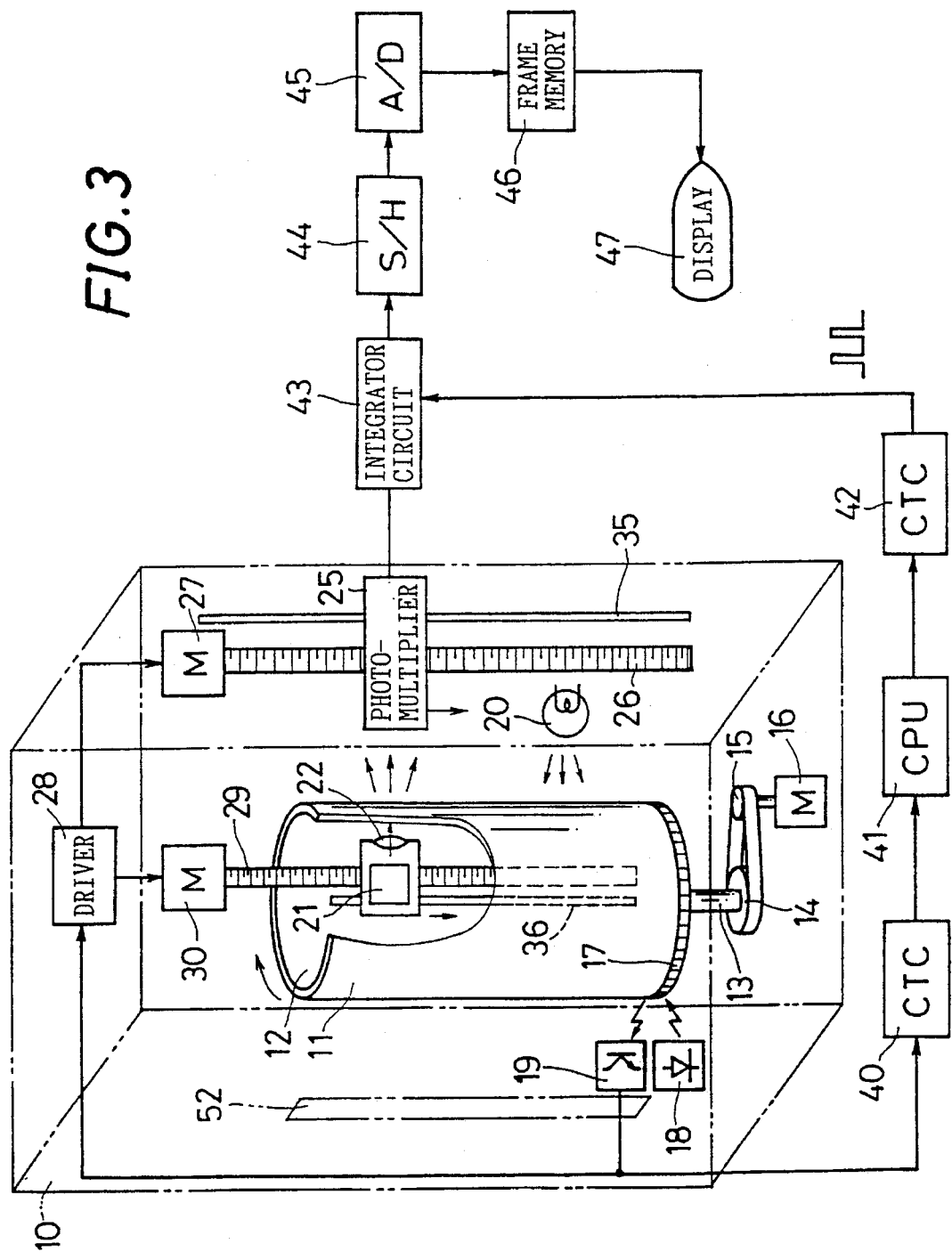
FIG. 3 is a view showing the construction of a second embodiment of the invention.

FIG. 3 is a view showing the construction of a second embodiment of the invention. In an X-ray imaging device 10, a storage fluorescent sheet 11 is provided on the circumstantial surface of a hollow, light-transmissive rotation drum 12. The shaft 13 of the rotation drum 12 is driven by a motor 16 via pulleys 14, 15. An optical encoder 17 having streaks at regular intervals is provided at a circumstantial surface end portion of the rotation drum 12. A photosensor composed of a photodiode 18 and a phototransistor 19 generates a pulse signal corresponding to the rotation angle of the optical encoder 17.

A laser 21, such as a semiconductor laser, is used as an excitation light source for irradiating the storage fluorescent sheet 11 with excitation light, and is mounted on a screw shaft 9 while being unable to rotate around a support member 35, yet slidingly movable in the axial direction of the shaft 29, and moved linearly at a constant speed in the axial direction of the rotation drum 12 by the rotation of a motor 30. The laser 21 is disposed inside the rotation drum 12 to make the X-ray imaging device 10 compact. The excitation light from the laser 21 is converged by a lens 22, passes through the light-transmissive rotation drum 12 and enters the inside surface of the rotation drum 12 nearly perpendicularly. Accelerated-phosphorescence emission is generated from the portion irradiated with the excitation light depending on the level of the X-ray energy stored in the storage fluorescent sheet 11, The accelerated-phosphorescence emission discharged from the rotation drum 12 is received by a photomultiplier 25 disposed close to the storage fluorescent sheet 11. An optical filter for shutting off the excitation light and allowing only the accelerated-phosphorescence emission to pass through is provided on the light-receiving surface of the photomultiplier 25.

The photomultiplier 25 is mounted on a screw shaft 26, while being unable to rotate, yet slidingly movable in the axial direction of the shaft 26 relative to a support member 35 and moved linearly at a constant speed in the axial direction of the rotation drum 12 by the rotation of a motor 27. The motor 27 and the motor 30 rotate in synchronization with each other so that the laser 21 is opposed to the photomultiplier 25 at all times to perform secondary scanning during reading. On the other hand, primary scanning during reading is performed by the rotation of the rotation drum 12. After the two-dimensional scanning of the storage fluorescent sheet 11 is completed, an eraser lamp 20 turns on, the rotation drum 12 rotates, and residual X-ray energy is erased from the entire surface.

The pulse signal from the photosensor is supplied to a motor driver 28 for driving the motors 27, 30 so as to operate the rotation drum 12 and the screw shafts 26, 29 in synchronization with each other. The pulse signal is also supplied to an integrator circuit 43 via a CTC (counter timer circuit) 40, a CPU (central processing unit) 41 and a CTC (counter timer circuit) 42.

The image signal converted into an electrical signal by the photomultiplier 25 is supplied to the integrator circuit 43 and integrated in synchronization with the above-mentioned pulse signal, sampled by an S/H (sample-and-hold) circuit 44, converted into digital data by an A/D (analog/digital converter) circuit 45, and then stored in a frame memory 46. The image data stored in the frame memory 46 is indicated on a display 47, such as a CRT (cathode ray tube).

Next, recording operation is described below. During X-ray imaging, the laser 21, the photomultiplier 25, the eraser lamp 20, etc. stop operating, and the rotation drum 12 makes one revolution at a low speed (in 15 seconds, for example) in synchronization with one revolution of the swivel member 2 shown in FIG. 1. This synchronization is performed so that the X-ray movement speed at the tomographic plane of the subject P is equal to the circumstantial surface movement speed of the rotation drum 12. As a result, the X-rays from a secondary slit 52 enter the X-ray imaging device 10, and a desired tomographic image is recorded on the storage fluorescent sheet 11.

Next, image reading operation is described below. The rotation drum 12 rotates at a high speed of 1024 rpm, for example, and the laser 21 and the photomultiplier 25 move by 0.1 mm, for example, as the rotation drum 12 makes one revolution. The X-ray energy stored in the storage fluorescent sheet 11 is converted into accelerated-phosphorescence emission by excitation light. The accelerated-phosphorescence emission is converted into an electrical signal depending on the intensity of the accelerated-phosphorescence emission by the photomultiplier 25. The tomographic image thus taken is read as a time series image signal, stored in the frame memory 46 as digital data, subjected to a desired signal processing and displayed.

After a series of reading operations, the eraser lamp 20 turns on, the rotation drum 12 rotates, and residual X-ray energy is released so as to be ready for the next X-ray imaging.

Third Embodiment

Figure 4:
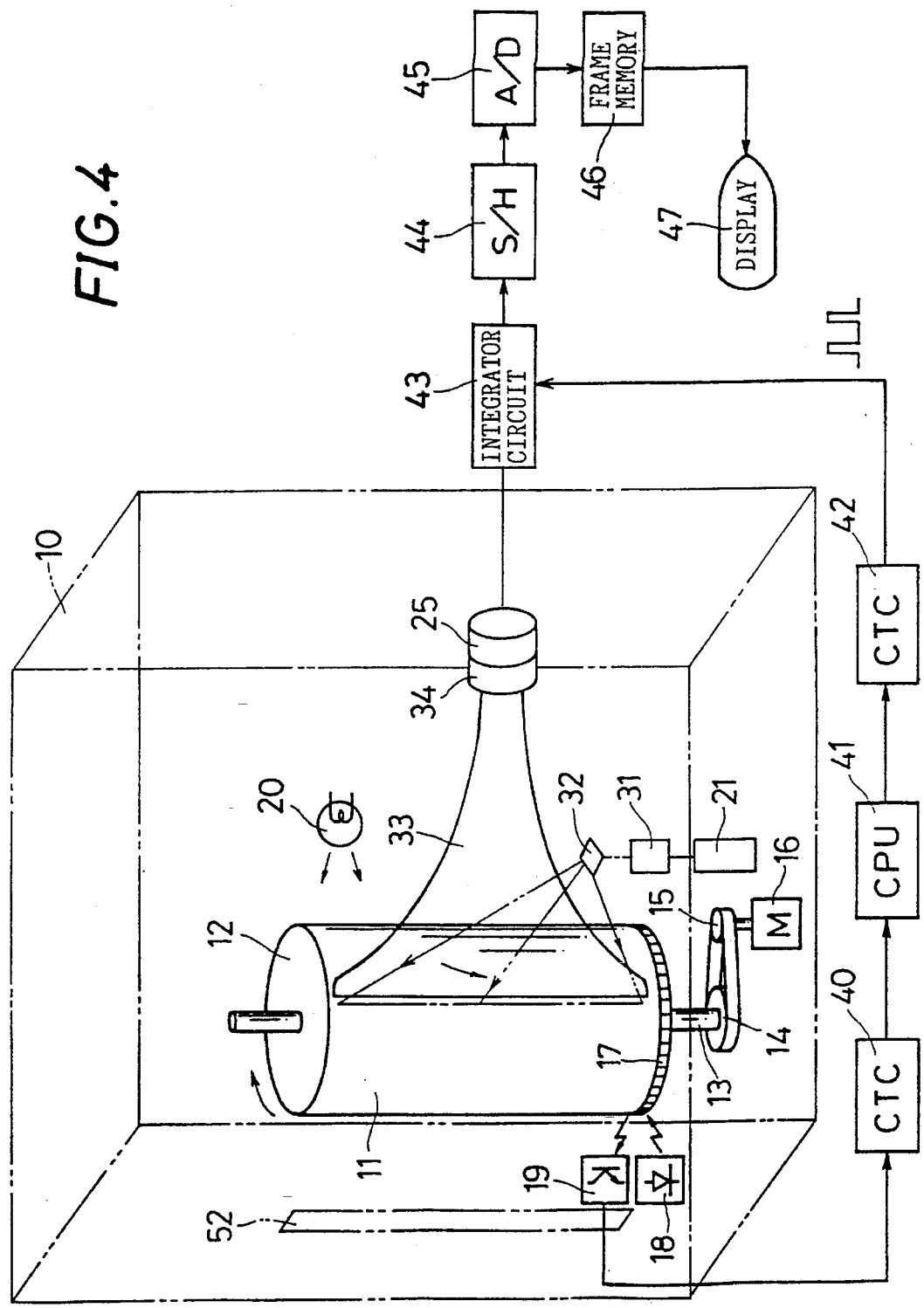
FIG. 4 is a view showing the construction of a third embodiment of the invention.

FIG. 4 is a view showing the construction of a third embodiment of the invention. In an X-ray imaging device 10, a storage fluorescent sheet 11 is provided on the circumstantial surface of a rotation drum 12. The shaft 13 of the rotation drum 12 is driven by a motor 16 via pulleys 14, 15. An optical encoder 17 having streaks at regular intervals is provided at a circumstantial surface end portion of the rotation drum 12. A photosensor composed of a photodiode 18 and a phototransistor 19 generates a pulse signal corresponding to the rotation angle of the optical encoder 17.

A laser 21, such as a semiconductor laser, is used as an excitation light source for irradiating the storage fluorescent sheet 11 with excitation light. The excitation light from the laser 21 is converged by a lens system 31, deflected at regular intervals by a scanning mirror 32, such as a vibratory mirror or a polygon mirror to perform scanning on the storage fluorescent sheet 11 in the axial direction of the rotation drum 12. Accelerated-phosphorescence emission is generated from the portion irradiated with the excitation light depending on the level of the X-ray energy stored in the storage fluorescent sheet 11. The accelerated-phosphorescence emission is converged by a fiber optic bundle 33, enters a photomultiplier 25 via an optical filter 34, and is converted into an electrical signal. The optical filter 34 has functions for shutting off the excitation light and allowing only the accelerated-phosphorescence emission to pass through.

In this way, primary scanning is performed by the scanning mirror 32. In addition, secondary scanning is performed by the rotation of the rotation drum 12. When the two-dimensional scanning of the storage fluorescent sheet 11 is completed, the rotation drum 12 rotates, an eraser lamp 20 turns on, and residual X-ray energy is erased from the entire surface.

The pulse signal from the photosensor is supplied to an integrator 43 via a CTC (counter timer circuit) 40, a CPU (central processing unit) 41 and a CTC (counter timer circuit) 42.

The image signal converted into an electrical signal by the photomultiplier 25 is supplied to the integrator circuit 43 and integrated in synchronization with the above-mentioned pulse signal, sampled by an S/H (sample-and-hold) circuit 44, converted into digital data by an A/D (analog/digital converter) circuit 45, and then stored in a frame memory 46. The image data stored in the frame memory 46 is indicated on a display 47, such as a CRT (cathode ray tube).

Next, recording operation is described below. During X-ray imaging, the laser 21, the photomultiplier 25, the erasure lamp 20, etc. stop operating, and the rotation drum 12 makes one revolution at a low speed (in 15 seconds, for example) in synchronization with one revolution of the swivel member 2 shown in FIG. 1. This synchronization is performed so that the X-ray movement speed at the tomographic plane of the subject P is equal to the circumstantial surface movement speed of the rotation drum 12. As a result, the X-rays from a secondary slit 52 enter the X-ray imaging device 10, and a desired tomographic image is recorded on the storage fluorescent sheet 11.

Next, image reading operation is described below. The excitation light from the laser 21 is scanned at a high speed by the scanning mirror 32. On the other hand, the rotation drum 12 rotates at a low speed, that is, moves by 0.1 mm, for example, as the scanning mirror 32 performs one scanning operation along the circumstantial surface of the rotation drum 12. The X-ray energy stored in the storage fluorescent sheet 11 is converted into accelerated-phosphorescence emission by excitation light. The accelerated-phosphorescence emission is converted into an electrical signal depending on the intensity of the accelerated-phosphorescence emission by the photomultiplier 25. The tomographic image thus taken is read as a time series image signal, stored in the frame memory 46 as digital data, subjected to a desired signal processing and displayed.

After a series of reading operations, the erasure lamp 20 turns on, the rotation drum 12 rotates, and residual X-ray energy is released so as to be ready for the next X-ray imaging.

In all the embodiments described above, the secondary slit 52 of the X-ray imaging device 10 is a vertically long opening, and the X-ray imaging device 10 except the secondary slit 52 is enclosed with an X-ray shielding member.

Figure 5:
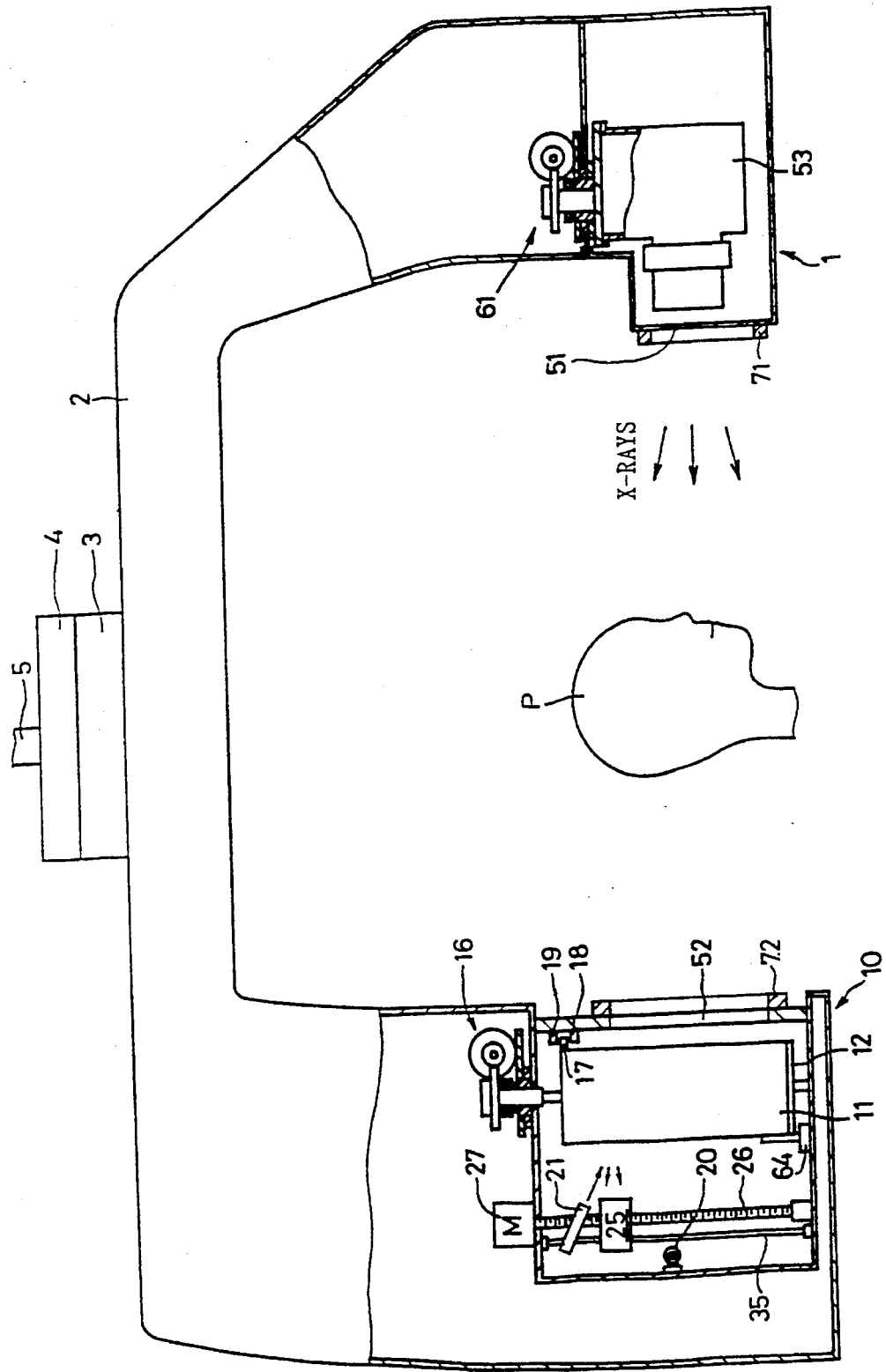
FIG. 5 is an overall view showing the construction of a forth embodiment of the invention.

FIG. 5 is an overall view showing the construction of a fourth embodiment of the invention. At both ends of a swivel member 2, an X-ray generator 1 and an X-ray imaging device 10 are disposed opposite to each other. The X-ray generator 1, composed of an X-ray tube 53, a primary slit 51, etc., irradiates subject P with an X-ray beam having a slit shape. The X-ray imaging device 10 receives an image of X-rays having passed through the subject P and records the X-ray image on a storage fluorescent sheet 11 having a cylindrical shape. The storage fluorescent sheet 11 has a circumstantial length of 300 mm and a width of 150 mm, for example, so as to have the same dimensions as those of the currently used X-ray panoramic film, and is provided on the circumstantial surface of the rotation drum disposed in parallel with the rotation shaft of the swivel member 2. The drum rotates at a low speed during X-ray imaging and rotates at a high speed during image reading.

The swivel member 2 is supported by a stationary arm 5 via a rotation table 3 and an X-Y table 4. The rotation position, rotation speed and rotation center of the swivel member 2 are controlled so that a tomographic image can be taken along a predetermined tomographic plane of the subject P.

The primary slit 51 is provided with a primary slit shape changing mechanism 71 comprising a slide mechanism, etc. For changing the opening shape of the slit 51. In the same way, the secondary slit 52 is provided with a secondary slit shape changing mechanism 72 comprising a slide mechanism, etc. for changing the opening shape of the slit 52.

Figure 6:
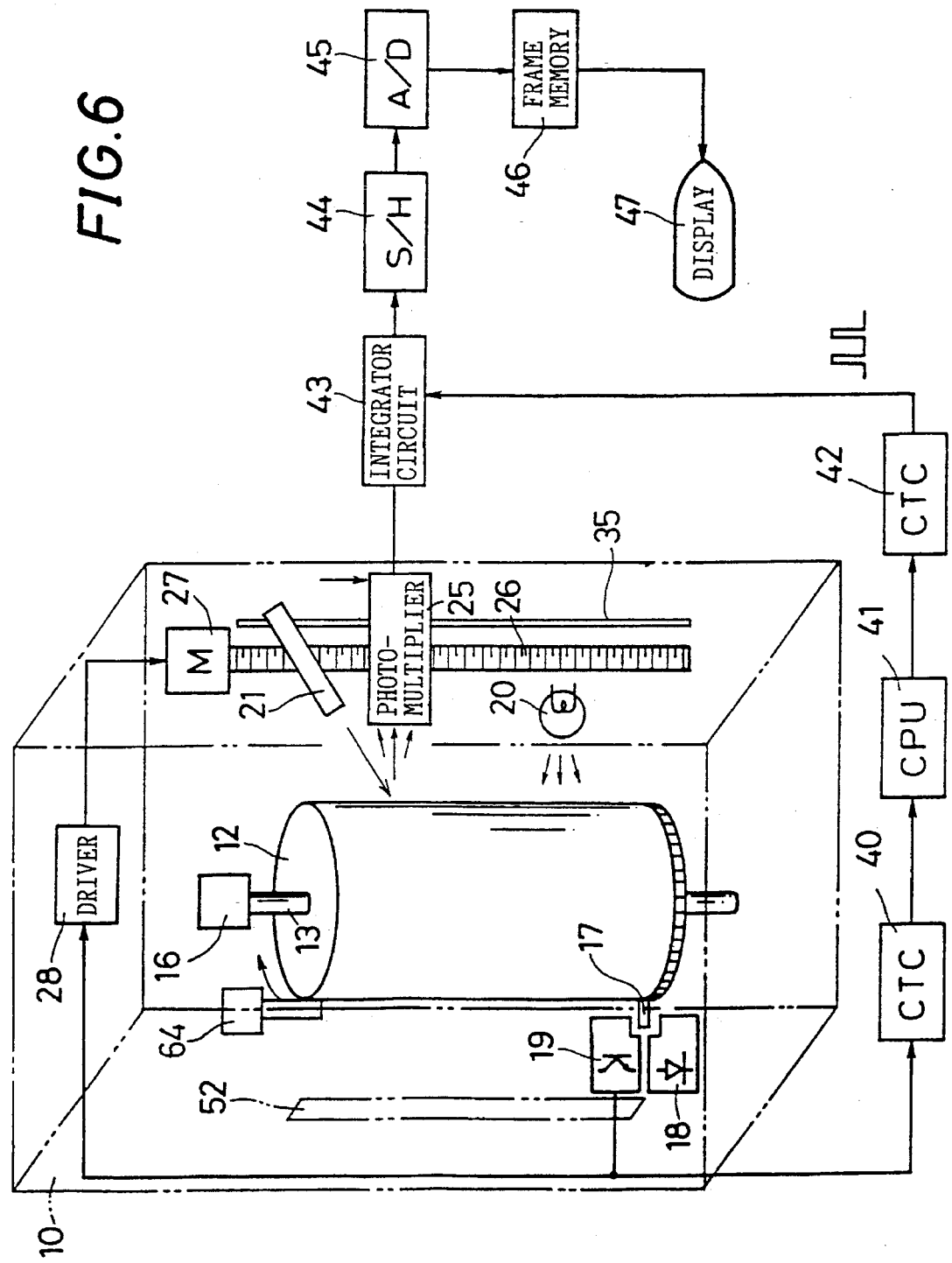
FIG. 6 is a view showing an X-ray imaging device 10 of FIG. 5.

FIG. 6 is a view showing an X-ray imaging device 10 shown in FIG. 5. In the X-ray imaging device 10, the storage fluorescent sheet 11 is provided on the circumstantial surface of the rotation drum 12, and the shaft 13 of the rotation drum 12 is rotated by a rotation mechanism 15. A detection member 17 for regulating the rotation start position of the rotation drum 12 is provided at a circumstantial surface end portion of the rotation drum 12. A photodiode 18 and a photo interrupter 19 generate a pulse signal corresponding to the imaging start home position of the rotation drum 12.

A laser 21, such as a semiconductor laser, is used as an excitation light source for irradiating the storage fluorescent sheet 11. The excitation light from the laser 21 is converged by a lens or the like and obliquely enters the storage fluorescent sheet 11 at nearly 45° with respect to the surface thereof. Accelerated-phosphorescence emission is generated from the portion irradiated with the excitation light depending on the level of the X-ray energy stored in the storage fluorescent sheet 11. The accelerated-phosphorescence emission is received by a photomultiplier 25 disposed close to the storage fluorescent sheet 11. An optical filter for shutting off the excitation light and allowing only the accelerated-phosphorescence emission to pass through is provided on the light-receiving surface of the photomultiplier 25.

The laser 21 and the photomultiplier 25 are engaged integrally and threadedly on a screw shaft 26, while being unable to rotate around a support member 35, yet slidingly movable in the axial direction of the screw shaft 26, and moved linearly at a constant speed in the axial direction of the rotation drum 12 by the rotation of a motor 27 to perform secondary scanning during reading. On the other hand, primary scanning during reading is performed by the rotation of the rotation drum 12 driven by a high-speed rotation motor 16 incorporated in a rotation mechanism. After the two-dimensional scanning of the storage fluorescent sheet 11 is completed, an eraser lamp 20 turns on and residual X-ray energy is erased from the entire surface, as the rotation drum 12 rotates.

The pulse signal from the photosensor is supplied to a motor driver 28 for driving the motor 27 so as to control the rotation drum 12 and the screw shaft 26 in synchronization with each other. The pulse signal is also supplied to an integrator circuit 43 via a CTC (counter timer circuit) 40, a CPU (central processing unit) 41 and a CTC (counter timer circuit) 42.

The image signal converted into an electrical signal by the photomultiplier 25 is supplied to the integrator circuit 43 and integrated in synchronization with the above-mentioned pulse signal, sampled by an S/H (sample-and-hold) circuit 44, converted into digital data by an A/D (analog/digital converter) circuit 45, and stored in a frame memory 46. The image data stored in the frame memory 46 is indicated on a display 47, such as a CRT (cathode ray tube).

Since the output of the photomultiplier 25 coincides with acoustic frequencies, the output may be recorded by a separate MD (mini-disc) recorder or a DAT (digital audio tape) recorder without any immediate signal processing.

Next, recording operation is described below. During X-ray imaging, the laser 21, the photomultiplier 25, the erasure lamp 20, etc. stop operating, and the rotation drum 12 is rotated by one revolution at a low speed (in 15 seconds, for example) in synchronization with the movement of the swivel member 2 by a low-speed rotation motor 64 having a built-in clutch. This synchronization is performed so that the X-ray movement speed at the tomographic plane of the subject P is equal to the circumstantial surface movement speed of the rotation drum 12. As a result, the X-rays from the secondary slit 52 enter an X-ray imaging device 310, and a desired tomographic image is recorded on the storage fluorescent sheet 11.

Next, image reading operation is described below. The rotation drum 12 is rotated by the high-speed rotation motor 16 at a high speed of 1024 rpm, for example, and the laser 21 and the photomultiplier 25 move by 0.1 mm, for example, as the rotation drum 12 makes one revolution. The X-ray energy stored in the storage fluorescent sheet 11 is converted into accelerated-phosphorescence emission by excitation light. The accelerated-phosphorescence emission is converted into an electrical signal depending on the intensity of the accelerated-phosphorescence emission by the photomultiplier 25. The tomographic image thus taken is read as a time series image signal, stored in the frame memory 46 as digital data, subjected to a desired signal processing and displayed.

After a series of reading operations, the eraser lamp 20 turns on, the rotation drum 12 rotates, and residual X-ray energy is released so as to be ready for the next X-ray imaging.

Figure 7:
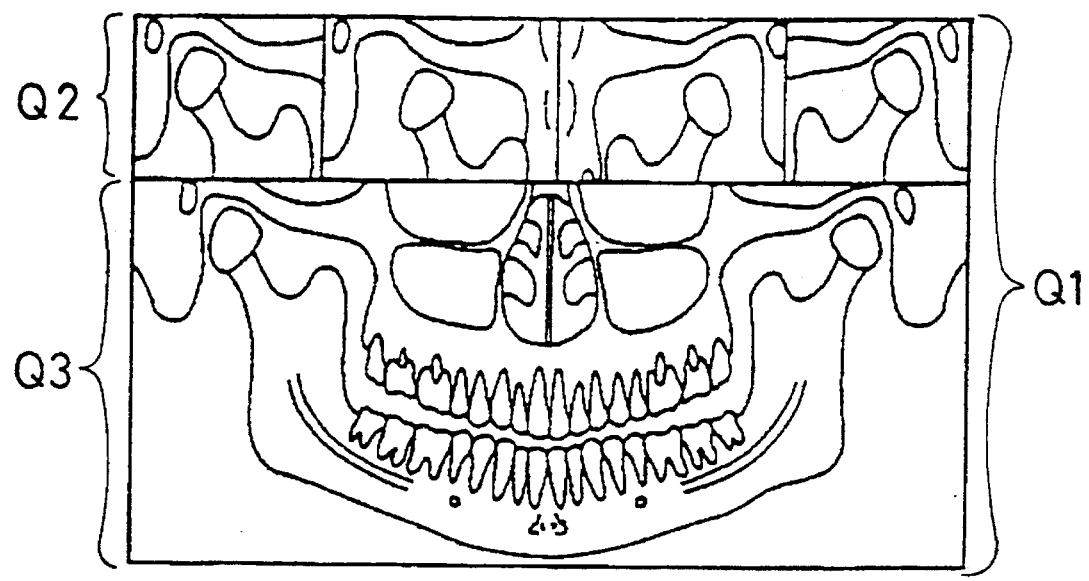
FIG. 7 is an illustration view showing some examples of imaging mode.

FIG. 7 is a view illustrating some examples of imaging modes. The panoramic imaging mode, temporomandibular joint imaging mode, etc. are available as imaging modes performed by using a digital panoramic X-ray apparatus. Image Q1 shown in FIG. 7 is a view obtained by developing the region of a single storage fluorescent sheet 11 that can be imaged. In the upper ⅓ portion of the region, four temporomandibular joint images Q2: an open-mouth condition image and a closed-mouth condition image of the right temporomandibular joint, and an open-mouth condition image and a closed-mouth condition image of the left temporomandibular joint are shown, and in the lower ⅔ portion of the region, a single panoramic image Q3 is shown.

These imaging operations are performed by properly adjusting the positional relationship between the patient P and the X-ray irradiation direction while regulating the opening shapes of the primary slit 51 and the secondary slit 52. When a sheet of X-ray film is used for a plurality of imaging operations in the case of imaging with a conventional X-ray film, the film is subjected to development processing after all imaging operations are completed. Therefore, it is necessary to complete all procedures even when only the panoramic image is desired to be observed earlier.

On the other hand, when X-ray imaging is performed by using the storage fluorescent sheet 11 just as in the case of the invention, the opening shapes of the primary slit 51 and the secondary slit 52 are changed in accordance with the imaging mode, such as the panoramic imaging mode or temporomandibular joint imaging mode, while the scanning region of the rotation drum 12 is changeable. As a result, since only the desired region of the storage fluorescent sheet 11 can be subjected to partial scanning and signal reading after X-ray imaging operation, the invention is advantageous in that necessary images can be obtained earlier. When reading only the third temporomandibular joint image from the left in FIG. 7, laser light is excited and accelerated-phosphorescence emission is received at the region corresponding to the image in accordance with the synchronization signal from the detection member 17 of the rotation drum 12. The panoramic image and the temporomandibular joint image are not necessarily required to be recorded on a single sheet as shown in FIG. 7, but may be recorded on two sheets.

Figure 8:
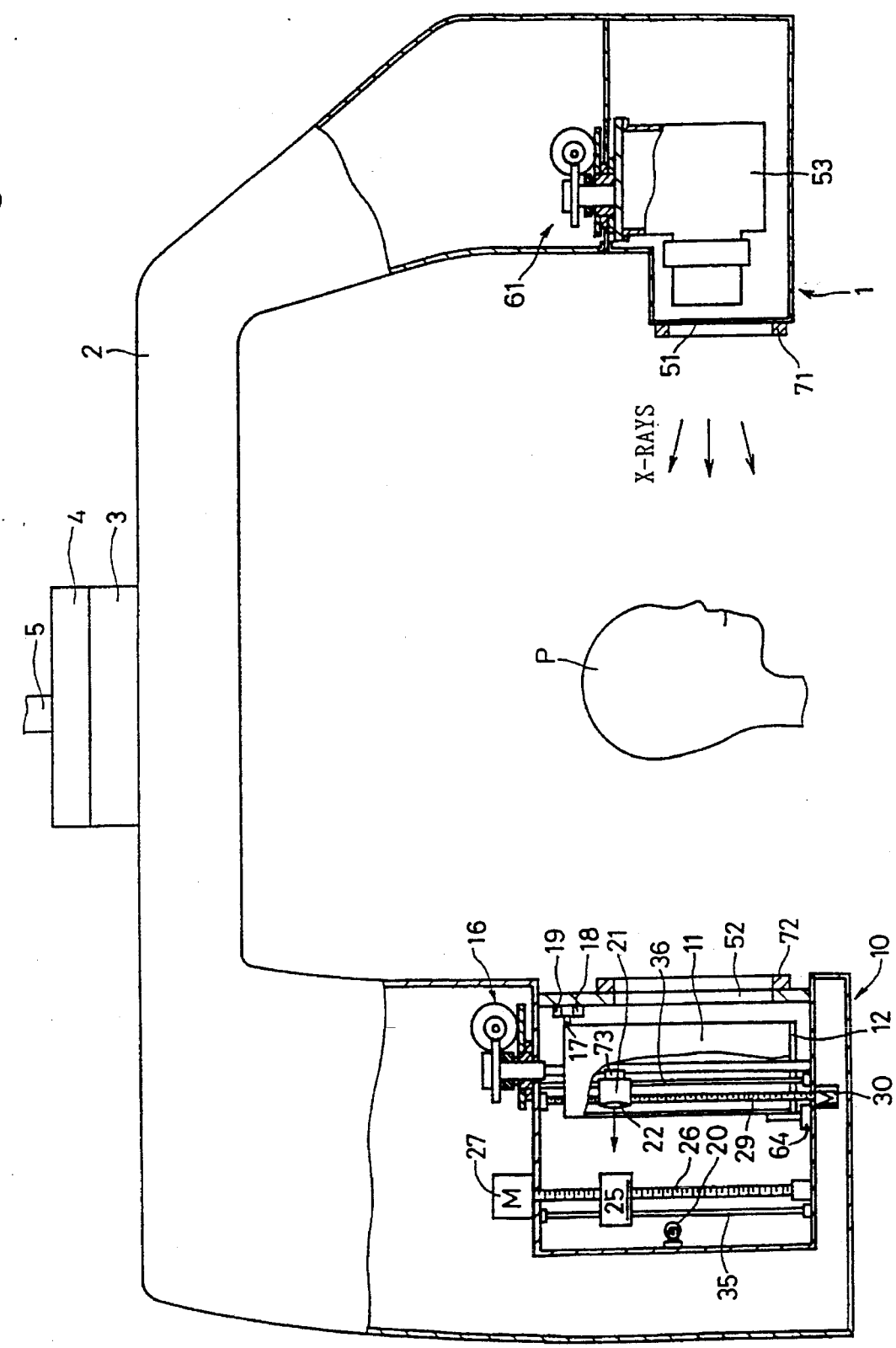
FIG. 8 is an overall view showing the construction of a fifth embodiment of the invention.

FIG. 8 is an overall view showing the construction of a fifth embodiment of the invention. Just as in the case shown in FIG. 5, at both ends of a swivel member 2, an X-ray generator 1 and an X-ray imaging device 10 are disposed opposite to each other. The X-ray generator 1 and the X-ray imaging device 10 are installed so as to be freely rotatable around the irradiation center axis extended between the X-ray generation portion and the X-ray detection portion.

In an X-ray imaging device 10, a storage fluorescent sheet 11 is provided on the circumstantial surface of a hollow, light-transmissive rotation drum 12, and the rotation drum 12 is rotated by a rotation mechanism. Another rotation mechanism 61 is used to cancel the opposed relationship between the X-ray generator 1 and the X-ray imaging device 10 at the time of cephalometric imaging.

A laser 21, such as a semiconductor laser, is used as an excitation light source for irradiating the storage fluorescent sheet 11 with excitation light and disposed inside the rotation drum 12. The excitation light from the laser 21 is converged by a lens 22, passes through the light-transmissive rotation drum 12 and enters the inside surface of the storage fluorescent sheet 11 nearly perpendicularly. Accelerated-phosphorescence emission is generated from the portion irradiated with the excitation light depending on the level of the X-ray energy stored in the storage fluorescent sheet 11. The accelerated-phosphorescence emission released outside the rotation drum 12 is received by a photomultiplier 25 disposed close to the storage fluorescent sheet 11. An optical filter for shutting off the excitation light and allowing only the accelerated-phosphorescence emission to pass through is provided on the light-receiving surface of the photomultiplier 25.

The photomultiplier 25 is mounted on a screw shaft 26, and moved linearly at a constant speed in the axial direction of the rotation drum 12 by the rotation of a motor 27. The laser 21 is mounted on a screw shaft 29, and moved linearly at a constant speed in the axial direction of the rotation drum 12 by the rotation of a motor 30. The motor 27 and the motor 30 rotate in synchronization with each other so that the laser 21 is opposed to the photomultiplier 25 at all times to perform secondary scanning during reading. On the other hand, primary scanning during reading is performed by the rotation of the rotation drum 12. After the two-dimensional scanning of the storage fluorescent sheet 11 is completed, an eraser lamp 20 turns on and residual X-ray energy is erased from the entire surface, as the rotation drum 12 rotates. Basic features of the X-ray imaging apparatus according to this embodiment are the same as those shown in FIG. 3.

Since the electrical configurations of the motor drive systems and the image signal processing system are similar to those shown in FIG. 6, they are not explained here.

On the rear side of the laser 21, that is, on the X-ray generator 1 side, an X-ray sensor 73 for measuring the intensity of X-rays having passed through the subject is installed. By feedback-controlling the dosage of X-rays generated from the X-ray generator 1 so that the ratio of the output from the X-ray sensor 73 to the output of rotation speed detectors (such as the photodiode 18 and the phototransister 19) may be constant, imaging is possible at a proper amount of X-ray exposure. Therefore, imaging errors, such as overexposure and underexposure, can be prevented securely, and the dosage of radiation exposure to patient P can be reduced. For the scanning mechanism of the X-ray sensor 73, the scanning mechanism of the laser 21 may also be used, as long as the scanning mechanism and the X-ray sensor 73 are inside the rotation drum 12. Alternatively, the scanning mechanism of the laser 21 may be provided independently. By using these kinds of scanning mechanisms, erroneous detection due to the presence of implants or metallic crowns disposed on teeth of patient P can be prevented, and in addition, the X-ray sensor 73 can be accurately positioned depending on a desirable imaging site of the patient P.

A representative example of the X-ray sensor 73 employs a fluorescence body, such as a fluorescent plate and a fluorescent sheet, which emits fluorescence upon exposure to X-rays in combination with a photoelectric conversion element, such as a photomultiplier, which converts the fluorescence emitted by the fluorescence body into an electric signal.

As for the X-ray sensor 73, the photomultiplier 25 in the foregoing example may also be used. In such instance, a moving mechanism equipped with a motor or the like is installed on the photomultiplier 25 so that during X-ray imaging, a fluorescent plate can be placed by the moving mechanism on the front side of the photomultipliter, and during image reading the fluorescent plate can be removed from the front side of the photomultipliter by the moving mechanism. Further, a photomultipliter 25 that is movable in the axial direction by the motor 27 may also be used as an X-ray sensor 73 with autoexposure control.

Figure 9:
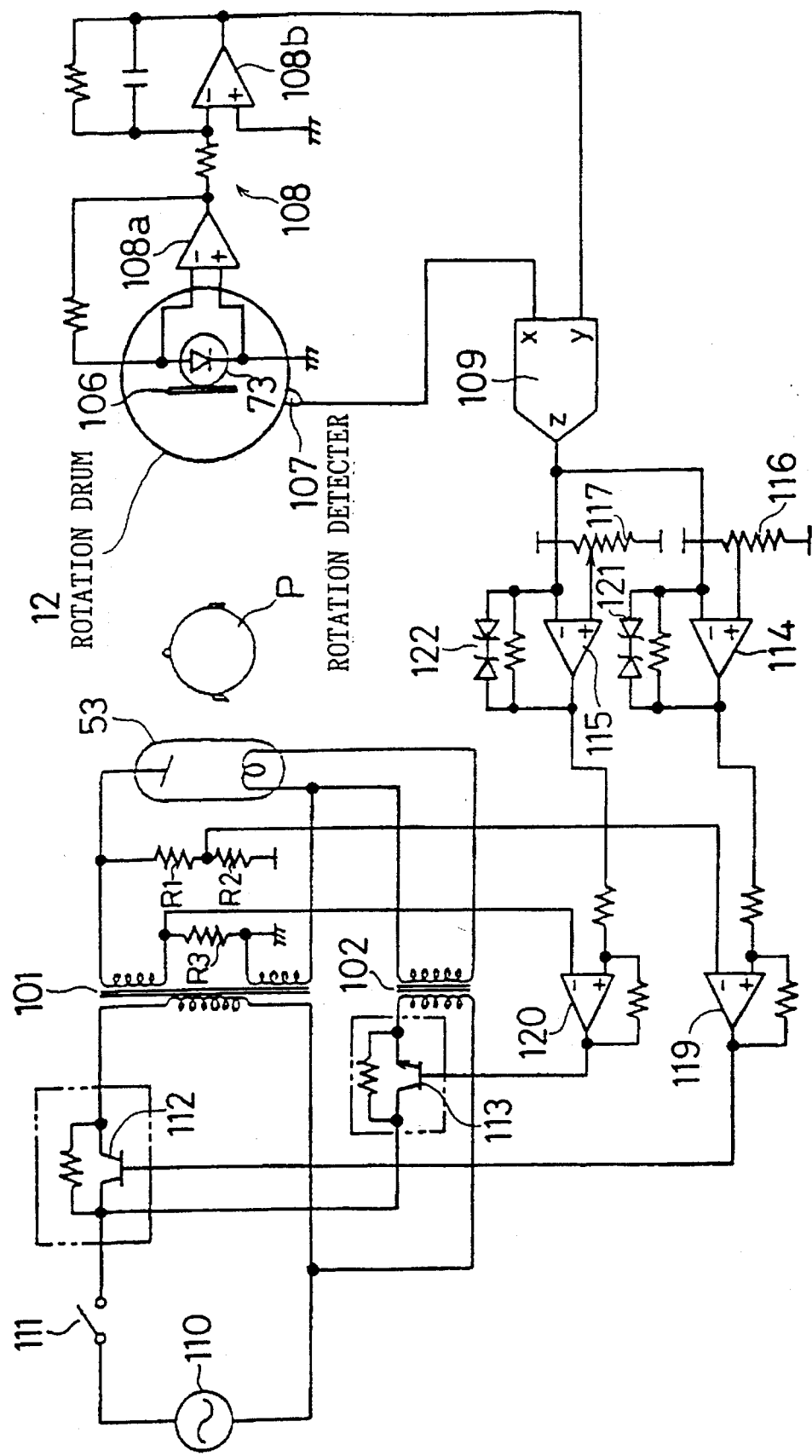
FIG. 9 is a block diagram showing an example of an X-ray autoexposure device incorporating an X-ray sensor 73.

FIG. 9 is a block diagram showing an example of the X-ray autoexposure control circuit which employs the X-ray sensor 73. The X-ray sensor 73 is, for example, comprised of a photodiode, and detects fluorescence from a fluorescent plate 106 and converts it into an electric signal. An outputted signal from the sensor 73 is amplified by a forward amplifier 108, comprised of amplifiers 108a and 108b, and is inputted into a divider 109 as a signal y.

On the other hand, a rotation detector 107 is installed in the rotation drum 12 and it outputs a signal corresponding to the number of rotation by the rotation drum 12, which is then inputted into the divider 109 as a signal y.

The divider 109 outputs a signal z by calculating the ratio of the signal x to the signal y (i.e., y/x). The signal z is supplied to a comparator 114 for controlling a tube voltage as well as to a comparator 115 for controlling a tube current. Limiters 114 and 115 are provided with limiters 121 and 122 which are comprised of Zener diodes and connected in parallel with the foregoing limiters, in their feedback resistance circuits.

The comparator 114 binary-processes the signal z on the basis of a standard voltage delivered by a standard voltage generator 116, and regulates, through an amplifier 119, an angle of conduction of a transistor 112 for the control of the tube voltage. The comparator 115 binary-processes the signal z on the basis of a standard voltage delivered by a standard voltage generator 117, and regulates, through an amplifier 120, an angle of conduction of a transistor 113 for the control of the tube current.

An AC power source 110 supplies a high voltage circuit consisting of the transistor 112 and a high voltage transducer 101 as well as a low voltage circuit consisting of the transistor 113 and a low voltage transducer 102 with electric power.

The high voltage transducer 101 supplies a high voltage to a spacing between an anode and a cathode of the X-ray tube 53, and the angle of its conduction is regulated by the transistor 112. The tube voltage of the X-ray tube 53 is partitioned to resistors R1 and R2, which is then feedback-inputted into the amplifier 119 to form a primary voltage negative-feedback loop.

The low voltage transducer 102 supplies a filament of the cathode of the X-ray tube 53 with a current for heating, and the angle of its conduction is regulated by the transistor 113. The tube voltage of the X-ray tube 53 is monitored by a voltage between both ends of a resistor R3, which is then feedback-inputted into the amplifier 120 to form a primary current negative-feedback loop.

As indicated above, the dosage of X-rays having passed from the X-ray tube 53 through the subject P is monitored by the X-ray sensor 73, and further, the number of rotation by the rotation drum 12 is monitored by the rotation detector 107. The autoexposure control of X-rays can be accomplished by controlling the tube voltage and the tube current of the X-ray tube 53 based on output signals from the X-ray sensor 73 and the rotation detector 107.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A digital panoramic X-ray imaging apparatus for performing tomographic imaging along a predetermined tomographic plane of a subject, said apparatus comprising:

an X-ray generator for irradiating a subject with X-rays;

an X-ray imaging device for detecting an image of X-rays having passed through the subject; and a swivel member for supporting the X-ray generator and the X-ray imaging device and for rotating the X-ray generator around the subject;

wherein the X-ray imaging device comprises a rotation drum disposed in parallel with a rotation shaft of the swivel member, a storage fluorescent sheet disposed on the circumferential surface of the rotation drum, an excitation light source for irradiating the storage fluorescent sheet with excitation light, a light receiving portion for receiving accelerated-phosphorescence emission generated from storage fluorescent sheet by excitation light irradiation, a rotation drive portion for performing primary scanning by rotating the rotation drum, and a linear drive portion for performing secondary scanning by moving the excitation light source and the light-receiving portion in the axial direction of the rotation drum.

2. A digital panoramic X-ray imaging apparatus for performing tomographic imaging along a predetermined tomographic plane of a subject, said apparatus comprising:

an X-ray generator for irradiating a subject with X-rays;

an X-ray imaging device for detecting an image of X-rays having passed through the subject; and a swivel member for supporting the X-ray generator and the X-ray imaging device and for rotating the X-ray generator around the subject;

wherein the X-ray imaging device comprises a light-transmissive rotation drum disposed in parallel with the rotation shaft of the swivel member, a storage fluorescent sheet disposed on the circumferential surface of the rotation drum, an excitation light source provided inside the rotation drum to irradiate the storage fluorescent sheet with the excitation light, a light-receiving portion provided outside the rotation drum to receive accelerated-phosphorescence emission generated from the storage fluorescent sheet by excitation light irradiation, a rotation drive portion for performing primary scanning by rotating the rotation drum, and first and second linear drive portions for performing secondary scanning by moving the excitation light source and the light-receiving portion in the axial direction of the rotation drum in synchronization with each other.

3. A digital panoramic X-ray imaging apparatus for performing tomographic imaging along a predetermined tomographic plane of a subject, said apparatus comprising:

an X-ray generator for irradiating a subject with X-rays;

an X-ray imaging device for detecting an image of X-rays having passed through the subject; and a swivel member for supporting the X-ray generator and the X-ray imaging device and for rotating the X-ray generator around the subject;

wherein the X-ray imaging device comprises a rotation drum disposed in parallel with the rotation shaft of the swivel member, a storage fluorescent sheet disposed on the circumferential surface of the rotation drum, an excitation light source for generating excitation light, a scanning optical system for irradiating the storage fluorescent sheet with the excitation light from the excitation light source and for performing primary scanning in the axial direction of the rotation drum, a light-receiving portion for receiving accelerated-phosphorescence emission generated from the storage fluorescent sheet by the excitation light irradiation, and a rotation drive portion for performing secondary scanning by rotating the rotation drum.

4. The digital panoramic X-ray imagine apparatus according to any of claim 1–3, wherein an X-ray sensor is disposed in the rotation drum and the dosage of X-rays generated from the X-ray generator is controlled depending on the output from the X-ray sensor.

5. The digital panoramic X-ray imaging apparatus according to any of claim 1–3, further comprising:

a primary slit for regulating an X-ray irradiation region in which a subject is irradiated with X-rays;

a primary slit shape changing means for changing the opening shape of the primary slit;

a secondary slit for regulating an X-ray detection region in which X-rays having passed through the subject are detected;

a secondary slit shape changing means for changing the opening shape of the secondary slit; and a scanning region setting means for setting the scanning region of the rotation drum, wherein the opening shapes of the primary and secondary slits and the scanning region of the rotation drum can be changed depending on the imaging mode.

* * * * *